(12) United States Patent
Chen et al.

(10) Patent No.: US 6,468,218 B1
(45) Date of Patent: Oct. 22, 2002

(54) 3-D ULTRASOUND IMAGING SYSTEM AND METHOD

(75) Inventors: Jian-Feng Chen, Issaquah; Dong-Chyuan Liu, Mercer Island, both of WA (US)

(73) Assignee: Siemens Medical Systems, Inc., Iselin, NJ (US)

( * ) Notice: Subject to any disclaimer, the term of this patent is extended or adjusted under 35 U.S.C. 154(b) by 0 days.

(21) Appl. No.: 09/944,865

(22) Filed: Aug. 31, 2001

(51) Int. Cl.$^7$ ............................................. A61B 8/00
(52) U.S. Cl. .................... 600/443; 382/128; 128/916
(58) Field of Search .................. 600/443; 128/916; 382/128

(56) References Cited

U.S. PATENT DOCUMENTS 5,594,807 A * 1/1997 Liu ............................. 382/128
5,793,883 A * 8/1998 Kim et al. ................... 382/128

* cited by examiner

Primary Examiner—Francis J. Jaworski
Assistant Examiner—Ruby Jain

(57) ABSTRACT

A 3-D region of interest (ROI) of a body is imaged, preferably using an ultrasound transducer. The intensity of an echo signal from each of a pattern of pixels within the ROI is measured and stored. The pixels are then grouped into pixel blocks, and the intensity values for the pixels in each sequentially selected current block are compiled in a current histogram. Each current histogram is compared with a reference histogram that corresponds to the distribution of echo signal intensities in a known region of speckle. A structure likelihood value is then computed based on the comparison, where the structure likelihood value indicates how likely it is that the current block corresponds to a structure of interest as opposed to noise. The intensity value for any pixel likely to be noise is preferably scaled down. The scaled intensity values are then projected, preferably using a maximum intensity projection, onto a 2-D display plane, a representation of which is then displayed for a user to see. The invention is able to image structures throughout the 3-D ROI even when they would otherwise be obscured by the speckle.

18 Claims, 3 Drawing Sheets

3-D ULTRASOUND IMAGING SYSTEM AND METHOD

BACKGROUND OF THE INVENTION

1. Field of the Invention

This invention relates to a system and corresponding method for generating and displaying a representation of a volume of a patient's body using ultrasonic imaging.

2. Description of the Related Art

In recent years, more and more effort has been directed towards developing and improving the ability of an ultrasonic imaging system to generate a displayable representation of three-dimensional regions of a patient's body. Unlike the already widely available 2-D imaging systems, which scan and image planes within the body, usually at constant depths; 3-D imaging systems compile imaging information for an entire 3-D region at a time.

Of course, existing display screens are 2-D, so that some 2-D subset (projection) even of 3-D data must be selected for display to the user. There are many different methods for creating a 2-D projection for display.

Three-dimensional imaging systems will, in many cases, allow visualization of body structures in a region of interest that cannot be imaged easily—or at all—using 2-D scanning. For example, assume that a blood vessel extends perpendicular to the scan plane. In 2-D scanning, this blood vessel will appear, at best, as a small ring. With 3-D scanning, as long as the 2-D projection is chosen properly, then the length of the blood vessel will be visible in the display. Another advantage of 3-D imaging is that it allows a given scanned volume to be examined (displayed) from different points of view.

Several different methods are known for selecting a 2-D subset of 3-D imaging data to be used for display. In other words, there are several different projection methods. According to one method, the system simply displays the image data that lies on a plane of intersection through the scanned volume. In other words, the system chooses a planar "slice" of the imaged volume. This can be done using traditional geometric algorithms.

One of the currently most popular projection techniques in 3-D ultrasound imaging is known as the Maximum Intensity Projection (MIP). According to this technique, a point of view is selected, which is usually the center of the piezoelectric array in the ultrasound probe. A projection plane is then selected, which is usually perpendicular to the centered normal of the array and is located between the array and the scanned volume. The plane is divided into an x-y grid of picture elements ("pixels"). A vector is then extended from the point of view through each pixel on the projection plane and into and through the 3-D pattern of imaged volume elements ("voxels") that make up the representation of the scanned volume. Each vector will pass through many voxels, each of which, in conventional B-mode imaging, is represented by a brightness value. In MIP imaging, the system determines the maximum brightness value lying on each vector, and then assigns that value to the pixel on the projection plane that the vector passes through. Of course, all of these processing steps are carried out in software, using known mathematical algorithms for computational geometry.

One of the advantages of MIP is that it does not require the user to choose the projection plane, that is, the displayed "slice" of the imaged volume. One problem that existing 3-D imaging systems face, however, as does any other type of signal-processing system, is noise.

Whenever an object is scanned by some form of radiation, structures within the object that are too small (more precisely, that are smaller than the wavelength of the scanning signal) to be resolved may still disperse, reflect, or otherwise interfere with the signal that is returned to the scanning device. When the imaging system then creates an image based on the returned scan signal, this interference, which is noise, often makes the image less clear.

In medical ultrasonic imaging, the ultrasonic beam transmitted into the body is scattered by the microstructure of the tissue. This interference effect is known as "speckle." Speckle causes the image to appear granular, which in turn obscures smaller structures and masks the presence of low-contrast lesions. The problem is analogous to "snow" on a television screen, which reduces the "sharpness" of the TV image.

Although ultrasonic images are corrupted by speckle, they contain a variety of features that should be preserved. Existing image filtering methods, however, typically introduce severe blurring in order to adequately suppress the speckle noise, which is composed of low spatial frequencies. In other words, these methods either "smooth" the parts of the image one wishes to keep sharp (the useful signal), along with smoothing out the noise, or they fail to eliminate noise that itself is relatively "smooth."

Several methods are known for addressing the problem of speckle. One drawback of most existing speckle-reduction methods is, however, that they are computationally intensive, even for the conventional 2-D imaging for which they are designed. Of course, the problem of computational complexity is much greater in the context of 3-D imaging, in which the number of image brightness values that must be processed will typically be several orders of magnitude greater than in 2-D imaging. This reduces the usefulness of such techniques for high-speed (preferably "real-time") imaging with high resolution and a correspondingly large numbers of pixels.

U.S. Pat. No. 5,594,807 (Liu, Jan. 14, 1997) describes a method and a system for adaptive filtering of ultrasound imaging data in order to remove speckle. In this system, a reference pixel (2-D) is selected, either by the user, or automatically, if possible, from an area of pixels that is assumed to lie in a region of speckle. The system then compiles a reference histogram of the various intensity ("brightness") values of the different pixels in the speckle region, grouped into bins. Then, the 2-D scan is performed as normal. The scanned 2-D region itself is partitioned into pixel regions. Brightness histograms are then computed for each pixel region. The histogram of each pixel region is then compared with the reference histogram. The more a pixel region's histogram matches the reference histogram, the more likely the system assumes it to represent speckle. The contribution (brightness) of pixel regions in the image displayed for the user is then weighted according to the estimated speckle likelihood, with regions of speckle suppressed.

One problem with the system described in U.S. Pat. No. 5,594,807 is that it still does not allow the user to view the 3-D structure of the ultrasonically scanned interrogation region. Returning to the example of a perpendicularly extending blood vessel, the system described in U.S. Pat. No. 5,594,807 would still represent the blood vessel as a ring, although, in most cases, with greater contrast than otherwise.

In the context of 3-D ultrasound imaging, a particularly troublesome consequence of speckle is that it can obscure specular structures of interest. If, for example, a region of speckle lies in the same direction relative to the point of view as, say, a baby's finger, and if the echo return from the speckle region is stronger than from the finger, then the speckle, that is, the noise, will be displayed rather than the more relevant structure, that is, the finger.

What is needed is an imaging system and method that eliminate or, at least reduce, the effect of speckle in 3-D ultrasound imaging and thereby improve the ability of the system to see body structures that would, in conventional systems, be obscured by speckle. This invention provides such a system and method.

SUMMARY OF THE INVENTION

The invention provides a system and a related method for imaging a region of a body. An imaging device, preferably an ultrasound transducer is activated so as to transmit spatially focussed beams of ultrasound or other form of energy into a three-dimensional (3-D) interrogation region (IR) of a body and to receive echo signals from a region of interest (ROI) within the IR. A three-dimensional (3-D) representation of the ROI is then generated as a 3-D pattern of image elements. An intensity value is then assigned to each image element, corresponding to a predetermined imaging property of the image element. Three-dimensional groups of the image elements are then selected at different positions within the ROI and a block property value is computed for each block, the block property values indicating the likelihood that the respective element block corresponds to a region of noise. The intensity values are then projected onto a two-dimensional (2-D) display plane as a function of the block property values and a representation of the display plane is then displayed on a display.

In the preferred embodiment of the invention, a current distribution function of the intensity values of the image elements is evaluated for each of the different blocks. Each block property value is then computed as a predetermined comparison function of the current distribution function and a reference distribution function.

The reference distribution function is preferably determined and evaluated first by selecting a reference region of known noise, preferably a region of known speckle. Reference noise intensity values, which are preferably representations of the intensity of ultrasonic echo return signals from speckle, are then measured from a plurality of points within the reference region. The reference noise intensity values are then grouped into a plurality of intervals that cover an intensity range from a minimum intensity to a maximum intensity. For each interval, a bin value is then assigned that is a count of how many of the reference noise intensity values that lie within the respective interval. The current distribution function is then preferably computed by grouping the intensity values of the image elements in a current one of the element blocks into the plurality of intervals and calculating a predetermined comparison function of the number of current intensity values and reference intensity values in each interval.

One computationally efficient and therefore preferred comparison function is a function of the absolute differences between the number of current intensity values and the number of reference intensity values in each interval. One example of the comparison function that may be used to advantage is a function of the sum of the squares of the absolute differences between the number of current intensity values and the number of reference intensity values in each interval.

In the preferred embodiment of the invention, if the block property value indicates that the element block corresponds to a region of noise, the intensity values of that element block are scaled down in order to reduce the likelihood that they will end up in and degrade the displayed image.

The preferred method for projecting the intensity values onto the 2-D display plane is a maximum intensity projection. (MIP) which entails selecting a point of view; projecting a plurality of vectors from the point of view and through the three-dimensional (3-D) representation of the interrogation region; and selecting for display on the display plane the image element whose intensity value is greatest along each respective vector.

The invention also provides for color-coding the display is order to even further help the user distinguish between noise and structure and to reduce the visible effect of imaged noise. In this embodiment of the invention, a color is associated with each of a plurality of block property value intervals. When the representation of the display plane is displayed, the system renders each image element displayed with the color associated with the block property value interval in which its corresponding block property value falls.

DETAILED DESCRIPTION

Introduction

The main idea of this invention is that a 3-D region of an interrogation is region of a patient's body is scanned. Return echo signals corresponding to speckle are then suppressed. This allows the system according to the invention to effectively "see through" even bright speckle so as to be able to image actual structures of interest that may be located behind it. The techniques by which the invention accomplishes this are described below. First, however, the main hardware and software components of the system according to the invention are explained.

Main System Components

Figure 1:
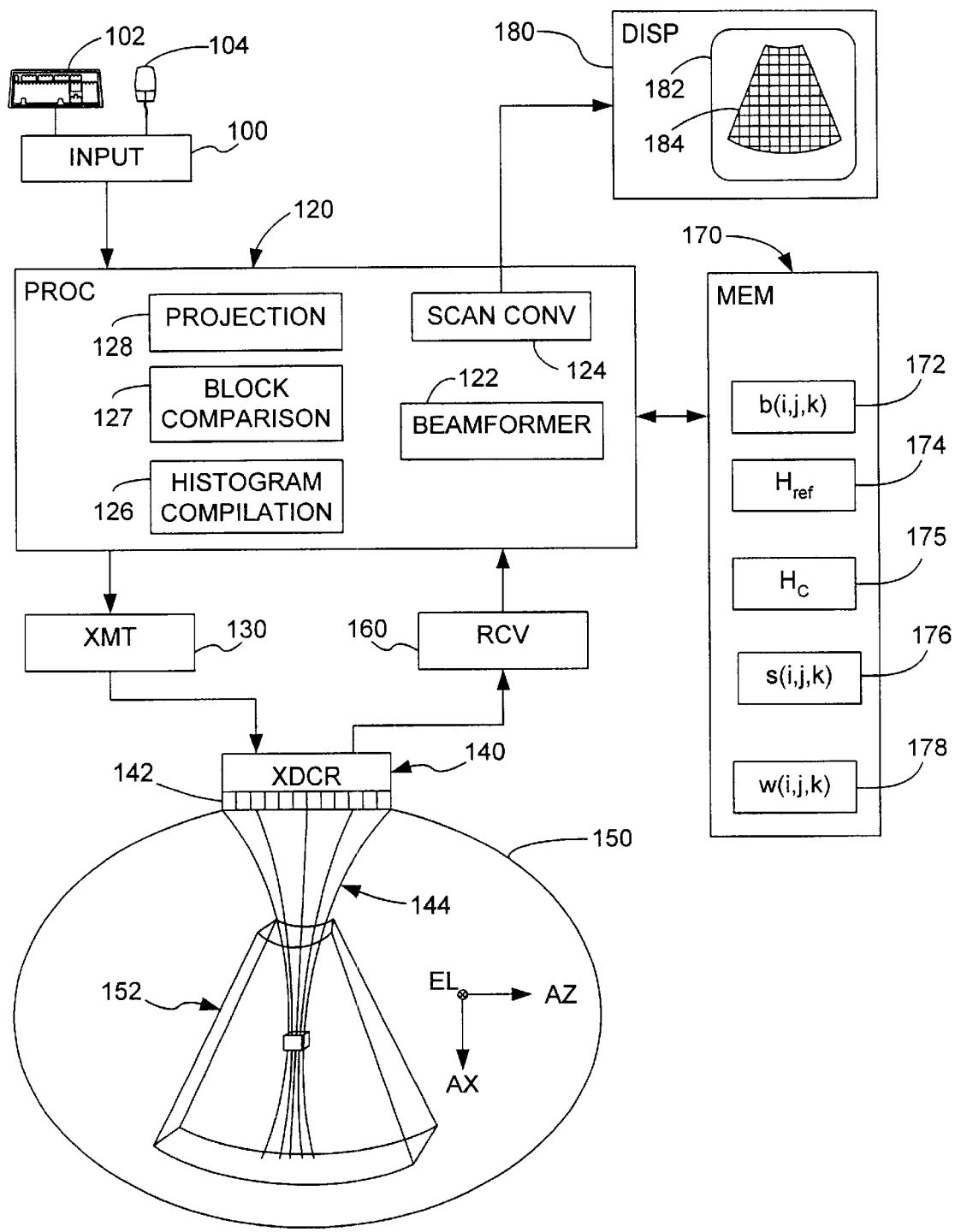
FIG. 1 is a block diagram illustrating the main components of the system according to the invention.

FIG. 1 illustrates the main components of an ultrasonic imaging system that is suitable for implementing the invention. The user enters various conventional scan parameters into an input unit 100, which typically comprises conventional hardware input ports and any necessary drivers within an operating system and which typically includes or is connected to such devices as a keyboard 102, knobs, a mouse 104, and/or buttons. The input unit is connected to a processing system 120, which will typically be an electrically connected and cooperating group of processors such as microprocessors and/or digital signal processors; the processing system may, however, also be implemented by a single processor as long as it is fast enough to handle the various tasks described below.

As in known systems, the processing system 120 sets, adjusts, and monitors the operating parameters of a conventional transmission control circuit 130. This control circuit 130 generates and applies electrical control and driving signals to an ultrasonic probe, that is, transducer 140, which includes an array 142 of piezoelectric elements. As is well known in the art, the piezoelectric elements generate ultrasonic waves when electrical signals of the proper frequency are applied to them.

By placing the probe 140 against the body 150 of a patient, these ultrasonic waves enter a portion 152 (an "interrogation region," or a "region of interest") of the patient's body. By varying the phasing, amplitude, and timing of the driving signals in a conventional manner, the ultrasonic waves from the respective array elements are formed into a transmit beam 144. The beam typically converges at a focal depth, beyond which it once again diverges. The transmit beam is steered (in the azimuth AZ and elevation EL directions) and focused in the axial AX, that is, depth, direction so as to concentrate the ultrasonic energy of the beam onto desired points within the interrogation region. In FIG. 1, for example, the beam 144 is shown as being steered just left of the array centerline, that is, the line that would extend from the center of the array and perpendicular to it.

The invention is not limited to ultrasound imaging, or to applications with active transducers that both generate the scanning signal and sense the return signal from the scanned region; rather, the invention may also be used where the transmitting device (which may be located within the interrogation region itself) or the device that induces a return signal from the region may be separate from the device that senses the return signal. Thus, the invention may be used to improve the quality of, for example, images from MRI, CAT and PET systems. Any needed modifications of the techniques described below will be well within the skill of those who design imaging systems using modalities other than ultrasound. Use of the invention in an ultrasound system is assumed here because it is the modality of a successfully tested prototype of the invention and is expected to be the most common area of use of the invention.

Similarly, the invention does not require any particular frame rate or processing speed. Using the preferred embodiment of the invention and a Siemens Elegra ultrasound imaging machine, however, real-time imaging, with all the advantages of the invention described below, has been shown to be possible. The invention may also be used for post-processing of previously acquired scan data.

When any point in the interrogation region 152 is insonified, the transducer is typically switched from the transmit mode to a receive mode. In the receive mode, ultrasonic energy from the waves created by the elements 142 is reflected back (back-scattered) as a return echo signal. As is well understood, the piezoelectric elements 142 in the array 140 then convert the small mechanical vibrations caused by the echo signal into corresponding radio-frequency (RF) electrical signals. Amplification and other conventional signal conditioning is then applied to the return signals by a reception controller 160. This processing includes, as needed, such known signal conditioning as time-gating, gain and diffraction compensation, etc., in order to identify the echo signals that correspond to each scanned element in the interrogation region. The type of conventional signal processing needed will in general depend on the particular implementation of the invention and can be chosen using known design methods.

The reception controller 160, all or part of which is normally integrated into the processing system 120 itself, converts the ultrasonic, radio-frequency (RF) return signals (typically on the order of a few to tens of megahertz) into lower frequency ranges for processing, and may also include analog-to-digital conversion circuitry. This is well known in the art of ultrasonic imaging. If not included in the reception controller 160 itself, the processing system 120 will include a beamformer 122 that converts the conditioned return signals into corresponding receive beams, each of which normally corresponds to the echo from a transmit beam.

In conventional B-mode scanning, each point within the interrogation region is represented as an intensity (brightness) value. Thus, each image element (referred to below as a "pixel") is typically assigned a gray-scale brightness that may vary from pure white (100% luminance) to pure black (0% luminance). The number of different gray tones that a pixel may have is determined by the size of the memory data word that holds the numerical brightness parameter for that pixel. For example, if pixel brightness values are represented using 8-bit data words, then it would be possible to represent $2^8$=256 different levels of grayness, with, for example, "255" corresponding to maximum displayable brightness and "0" corresponding to maximum displayable darkness. The value "128" would in this case correspond roughly to "medium gray." Similar schemes may be used to create a color display, in which, instead of by luminance alone, increased signal strength from pixels is represented by increased chroma or hue, or by more red and less blue, or by using any other conventional color-coding scheme. What is of importance to this invention is that the entire 3-D interrogation region 152 can be represented as a discretized pattern (matrix) of brightness or signal intensity values, which are stored as frame brightness data $b(i,j,k)$ in a portion 172 of a memory 170.

The invention is not limited to any particular maximum number of pixels and the minimum number of pixels necessary to use the invention will become clear below. In the figures, each pixel is shown as being a cube merely for the sake of clarity and because a pixel is usually taken to represent a roughly orthogonal sub-set of the interrogation region space. The invention is also not limited to any particular pixel shape although, in order to maintain convenient indexing, it is computationally advantageous if the pixels are evenly or at least regularly distributed according to some set of coordinate axes such as the AX-AZ-EL axes of FIG. 1, or, equivalently, the i-j-k index directions shown in FIG. 3.

The interrogation region 152 is normally not in the same shape as what the user wants to see displayed; even when it is, the digital acoustic intensity values that make up the frame data are normally not in a form suitable for driving a conventional gray-tone or color display directly. The acoustic intensity values for a selected 2-D sub-set (scan plane) of the 3-D interrogation region are therefore applied to a conventional scan converter 124, which converts the digital acoustic values into display intensity values that are suitable for use in driving a display device 180.

The display device 180 typically includes or is connected to a conventional display driver and includes a screen 182 (for example, LED or CRT) that is divided into an X-Y (or polar) matrix or pattern of picture elements or "pixels" that make up an image 184 that the user can view and interpret. Note that a displayed image element will often be made up of more than one pixel, but that this will depend on the relative resolutions of the scan and of the display. The invention does not require any particular relative resolution.

As FIG. 1 shows, the processing system according to the invention also includes software modules 126, 127 and 128 for histogram compilation, block comparison, and 3D-to-2D projection, respectively. All or any of these modules, which may be implemented as sub-routines of a single body of code, may be designed using well-known programming techniques given the description below of the method according to the invention. The processing system 120 will include any hardware support for these modules as needed, for example, specialized co-processors designed for maximum speed in performing the various calculations and operations described below.

Pixel Blocks

In the most common applications of ultrasonic scanning, with linear arrays, the interrogation region 152 is scanned beamline-by-beamline. In conventional systems, the interrogation region is scanned as a pattern of 2-D planes in order to generate 2-D image information. The primary area of use of this invention is, however, three-dimensional imaging, so that the interrogation region should be scanned so as to compile, for the respective pixels $p(i,j,k)$, the 3-D pattern of brightness values $b(i,j,k)$. These values correspond to the intensity of the ultrasonic return echo signals from focus points within the interrogation region as the transducer array 140 is steered in azimuth and elevation, and focused axially at different depths. The manner in which this is done is well known in the art of ultrasonic imaging and is therefore not discussed in greater detail here. The invention may also be used with 2-D arrays.

Figure 2:
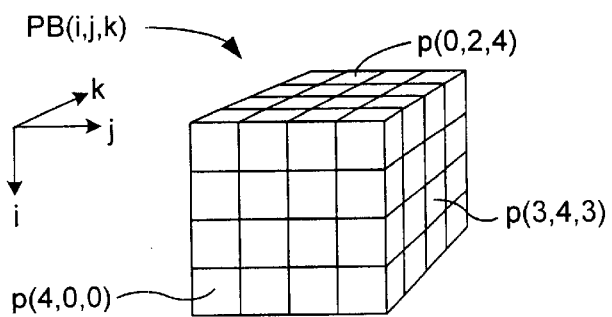
FIG. 2 illustrates a 3-D pixel block.

As is explained further below, the imaging method according to the invention operates primarily on groups of l×m×n pixels, referred to here as "pixel blocks" or "element blocks." FIG. 2 illustrates one such pixel block made up of a 4×4×4 volume of pixels. This block size proved to contain enough pixels to provide statistically significant and satisfactory results (explained below) without needlessly increasing the computational burden of the invention.

Any other pixel groupings may also be chosen to constitute blocks; the choice can be made using normal experimental methods, taking into account such factors as the resolution of the ultrasound scan (the separation between adjacent pixels), the size of the interrogation region, and the frame rate in relation to the computational burden of having larger pixel blocks. For example, a block might consist of 5×5×5 pixel groups, which would have the advantage that each block would have a center pixel, which may make indexing easier, but with the increased computational complexity caused by having almost twice as many pixels per block as a 4×4×4 block. It is also not necessary for the pixel blocks to have the same number of pixels in each dimension, although doing so will normally maximize the amount of local information used and will better conform to the assumption that the statistical properties of speckle are isotropic.

One way to form pixel blocks for the sake of histogram compilation and structure likelihood determination (described below) is to select each pixel in the interrogation region sequentially, to designate it as a current base pixel, then to temporarily group it with other pixels in a predetermined volume that includes the current base pixel. The calculations described below are then performed for the current base pixel. Thus, in FIG. 2, pixel block $PB(i,j,k)$ is the block associated with (for example, having as its center, or corner), the pixel at position $(i,j,k)$, which has a brightness value of $b(i,j,k)$.

The best block size for any given application will depend on the resolution of the image—the lower the resolution, the larger the block may have to be for it to be statistically meaningful. Block size will also depend on the achievable computation speed (depending on the speed of the processor, real-time image processing may not be possible if the block is chosen to be too large), and can be determined by normal calculation and experiment. Much of the uncertainty about the best block size is eliminated by using the preferred pre-calibration of each transducer using a phantom (described below).

In order to save computation time, it would also be possible for the system to group all the pixels in the interrogation region into pixel blocks and then to operate only on entire blocks. In other words, the interrogation region could be represented as a "block space" instead of as an "element space." This would reduce the computational burden by a factor at least approximately equal to the number of pixels in a block, but would of course reduce resolution. The choice will depend on required resolution and available processing speed and capacity. Below, merely by way of example, it is assumed that the system is fast enough to adjust each pixel in the interrogation region individually. The changes (mostly in indexing) needed to use the system for common adjustment of entire blocks will be obvious to anyone who has understood the method described below.

Speckle Reference

According to the invention, information within each pixel block is compared mathematically with information corresponding to known or assumed speckle regions. The more similar the information in the current block is to the speckle information, the more the system assumes that the current block itself lies in a region of speckle and the more it is suppressed. In order to perform such a mathematical comparison, there must first be something to compare current pixel blocks with.

Because the occurrence and properties of speckle depend mostly on the wavelength of energy used for scanning and on the particular transducer used and less on the type of tissue scanned, speckle can be assumed to have the same characteristics regardless of where in the interrogation region it occurs. Accordingly, according to the invention, a reference volume of representative tissue displaying no or at most little structure is therefore first scanned using the transducer 140. The reference volume may be of any desired size, as long as it does not include any significant structure. In particular, it does not need to be of the same size as the pixel blocks.

Let $r(u,v,w)$ be the set of brightness values sensed by scanning the reference volume. There will thus be $n=U*V*W$ reference brightness values, where U, V and W are the number of pixels in the u,v and w directions, respectively. Assume merely by way of example that each brightness value is represented by one byte, that is, by an eight-bit data word. Thus, each $r(u,v,w)$ is an integer from 0 to 255. If n is larger than 255, then there will be at least two reference pixels that have the same brightness value. In general, however, unless n is very much larger than 255, a grouping of values according to individual, specific brightness levels will not display enough variation to be statistically meaningful because the histogram showing the number of pixels having each of the 255 possible values will be substantially "flat" even in brightness intervals having many representatives.

In order to avoid this phenomenon, and to accumulate a histogram with a shape that provides statistically significant information (discussed below) about the reference block, the possible pixel brightness values are therefore preferably grouped into intervals or "bins" by a histogram compilation module 126 in the processing system 120. The number of bins one chooses, that is, that one sets the module 126 to use, represents a trade-off between noise tolerance and sensitivity: More bins will be more sensitive but less noise tolerant. The number of bins used will determine the smoothness of the histogram and can be determined by calculation and experiment for any given application. It will normally be advantageous if the number of bins is chosen to be a power of two because the number of bins will then usually divide evenly into the number of possible pixel brightness values, which will also typically be a power of two.

One example of bins and value distribution has 8 bins, each of which corresponds to an interval of 256/8=32 brightness values. Thus, in this example, measured pixel values in the reference block were assigned to bins as follows:

| Pixel brightness | Bin |
|---|---|
| 0–31 | 0 |
| 32–63 | 1 |
| 64–95 | 2 |
| 96–127 | 3 |
| 128–159 | 4 |
| 160–191 | 5 |
| 192–223 | 6 |
| 224–255 | 7 |

Of course, the number of bins (which do not have to represent equal intervals) may vary from application to application, and may be chosen using normal experimental methods.

Figure 3:
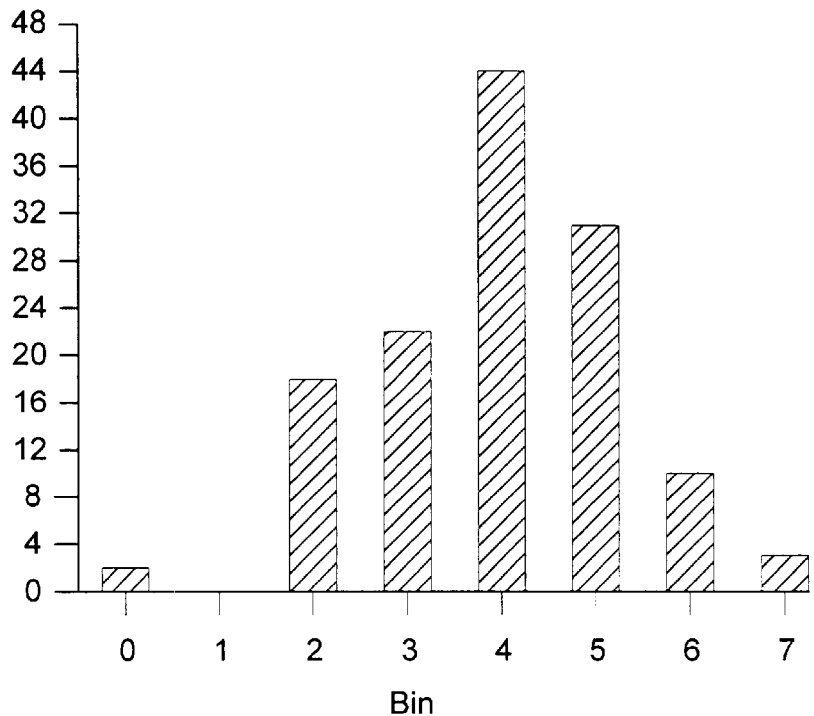
FIG. 3 is an illustration of a reference histogram.

An example of how the distribution of brightness values per bin might appear as a result of an ultrasound scan of a speckle region is illustrated as the histogram in FIG. 3, where the frequency of pixels in each bins is as follows:

| Bin | Pixel count |
|---|---|
| 0 | 2 |
| 1 | 0 |
| 2 | 18 |
| 3 | 22 |
| 4 | 44 |
| 5 | 29 |
| 6 | 10 |
| 7 | 3 |

In this sample, the reference block is assumed to consist of 8×4×4=128 pixels, which is the size used in a prototype of the invention. The chosen reference bock was not symmetric in order to take into account the property of most conventional ultrasound transducers that they have much better resolution in the axial (deoth) direction than in either the azimuth or elevation directions. This size is assumed here simply because it is easy to illustrate; in order to increase reliability, actual reference locks may be much larger, especially if they are pre-complied using a phantom (see below).

There are different ways to compile the reference histogram $H_{ref}$. In the preferred embodiment of the invention, each transducer that is to be used in a system that includes the invention is calibrated by using it to image a tissue-mimicking phantom, which may be designed using normal methods, to simulate or at least include clearly identifiable, homogeneous regions of speckle. The results of each such calibration correspond to a reference histogram. Because this calibration may be performed as a preliminary step, the size of the reference volume (block) may be of any size, and as much time can be taken as needed to compile a reliable reference histogram $H_{ref}$. Once the reference histogram $H_{ref}$ has been compiled, the corresponding values (frequency per bin) are stored in a corresponding memory space 174.

If this calibration step is done as part of the routine testing of the transducer after manufacture, then the data describing the histogram can be included as part of the transducer-specific specifications given to the user when the transducer is put into service. This would allow for testing and verification of the transducer later on, and even recalibration of the transducer, followed by storing of the updated $H_c$ in memory space 174.

Moreover, many reference scans of the speckle phantom may be performed and the results can be compared. If the results are consistent, for example, if the maximum or average standard deviation of the number of values in the respective bins is less than a predetermined threshold, then the histograms may be compiled, for example, by taking the average value for each bin, into a single reference histogram $H_c$ for that transducer.

It would also be possible to compile the reference histogram during the actual ultrasound scan in which it is to be used, although this will depend much more on the skill of the user. In this case, while viewing a conventionally generated display of the interrogation region, the user maneuvers an on-screen cursor using the mouse 102 (or equivalent) until the cursor on the display appears over or at least very near a portion of the display that appears to be a region of speckle. The user can then indicate that the corresponding pixel is to be used as the reference pixel either by a conventional keyboard entry or by activating some selector such as a mouse button or dedicated simple switch.

The histogram compilation module 126 then retrieves from the existing frame memory the brightness values for the pixels located within a predetermined region, that is, for a reference pixel block of predetermined dimensions. These brightness values are then assigned to bins as above, thereby forming the reference histogram $H_{ref}$ that can be used in the subsequent calculations.

The size of the reference pixel block may be predetermined and fixed, or it may be chosen automatically or manually for each image or sequence of images. The reference block should in any case include enough pixels that the brightness histogram is statistically meaningful: The window should be large enough that it includes some speckle, but ideally not so large that it includes regions of the image that indicate structure.

In the context of medical ultrasonic imaging, in order to have reliable speckle statistics, the reference block should be big enough to cover a region with a high density of scatterers. Tuthill, et al., have shown in "Deviation from Rayleigh statistics in ultrasonic speckle," 10 Ultrasonic Imaging 81–89, 1988, that the density of scatterers should be at least 5 per pulse width in order to approach a fully developed speckle region with Rayleigh distributions. The pulse width $\Delta T$ is defined by $4*\sigma$ where $\sigma$ is the Gaussian standard deviation of a Gaussian-enveloped pulse in the time domain. For a scanning depth of Z mm and N pixels in the axial direction, after conventional scan conversion, the minimum size m in the axial direction should therefore be $m=(N*\Delta T*C_0)/(2Z)$, where $C_0$ is the speed of sound.

Current Histograms

Once the reference histogram is compiled and stored in memory space 174 by the module 126, the system is ready for use in an actual scan. As is mentioned above, this scan will involve sequentially measuring the return signal strength (corresponding to the displayed brightness) from the different pixels p(i,j,k) in the interrogation region. For each corresponding pixel block PB(i,j,k) throughout the interrogation region, the histogram compilation module 126 then compiles a current histogram $H_c$ in the same way the reference histogram $H_{ref}$ is compiled: It assigns the brightness values b(i,j,k) to the various bins. For each pixel block, two histograms will thus be available—the common reference histogram $H_{ref}$ and the current histogram $H_c$, which is stored in a corresponding memory space 175.

In implementations of the invention, there is no need to actually display any histogram; actual graphically illustrated histograms are shown in the drawings for the sake of clarity only. In this description of the invention, "histogram" is therefore to be understood as meaning the accumulation into a number of memory positions (for example, in memory spaces 174, 175) of the number of pixels whose brightness (or other) values fall in the range assigned to the corresponding memory position. "Bins" of histograms are thus the memory positions. Histograms will normally be vectors (linked series of memory positions) whose elements are the "bins."

Histogram Comparison

U.S. Pat. No. 5,594,807 describes in detail how two histograms—one representing distribution statistics for a 2-D (rather than 3-D as in this invention) speckle reference region and another representing brightness distribution statistics for a current 2-D scan region—may be compared and their degree of similarity quantified. Identical or similar methods may be used in this invention. These techniques are repeated or summarized here for the sake of completeness. In general, comparison of the current histogram with the reference histogram involves normalization, peak registration and comparison.

Figure 4:
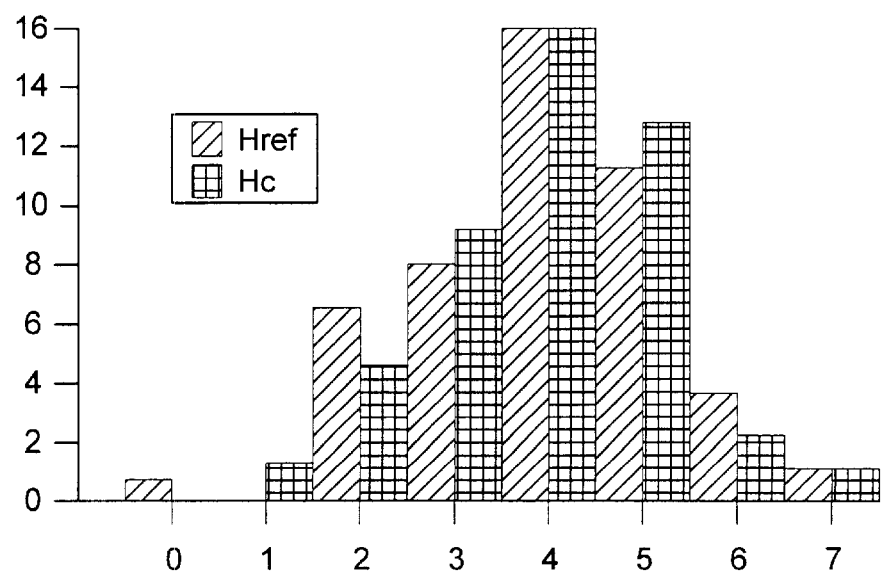
FIG. 4 illustrates comparison of imaging information from a current pixel block with that from a reference volume known to represent noise.

In order to establish a uniform scale for comparison of different histograms, each value of the reference histogram $H_{ref}$ (and later, each current histogram $H_c$) is preferably normalized. One way to normalize each histogram is to divide the value in each bin by the total number of pixels in a pixel block, that is, represented in the entire histogram and then to scale the result over some interval that allows for efficient digital computations. In FIG. 4, for example, both the reference histogram $H_{ref}$ and a current histogram have been normalized so that their "peaks" have a value of 16. Note that normalization need not be limited to linear scaling, although this simple normalization scheme will usually be adequate for use in this invention.

Because of tissue attenuation, two different portions of the interrogation region with identical acoustic characteristics will typically return different signals.

Specifically, the signal that takes a longer time (located deeper) to pass through intermediate tissue will appear "scaled down" relative to the other; in other words, it would appear uniformly more or less bright than the other, and by roughly a constant factor. Conventional "time gain compensation" (TGC) attempts to compensate for attenuation that occurs between the transducer and the interrogation region. Because the TGC function included in a system such as an ultrasonic imaging system is typically independent of frequency, it can only partially compensate the attenuation loss through tissue. In order to offset the effects of incomplete attenuation compensation after the TGC, each current histogram $H_{ref}$ and $H_c$ is therefore preferably shifted so that its "peak" (bin in which the most brightness values fall) coincides with the peak of the reference histogram $H_{ref}$. Thus, in FIG. 4, the current histogram $H_c$ has been shifted so that both its peak and the peak of the reference histogram $H_{ref}$ are aligned in bin 4 (that is, indexed identically for later calculations).

Once the reference histogram and current histogram have been compiled, normalized, and aligned, a degree of similarity between the two can be computed. There are many ways to quantify this similarity. Let $H_{ref}(i)$ and $H_c(i)$ be the values of the respective histograms in bin i, and let $S=S(H_{ref}, H_c)$ be a measure of similarity between $H_{ref}$, $H_c$.

One measure of similarity is the sum absolute difference between the two histograms. Thus, in this case:

$$S=\text{SUM}(\text{ABS}(H_{ref}(i)-H_c(i)), \text{ summed over all } i;$$

The more similar the two histograms are, the lower S will be. If the histograms are identical, then S=0. The maximum value of S will be the total number of values in each histogram. If it is desired to have a similarity measure in a range such as [0,1], S can of course itself be normalized to this range.

Another possible similarity measure would involve the second moment of the differences, that is, the statistical variation as opposed to just the absolute differences (first moment). In this case:

$$S=\text{SUM}(H_{ref}(i)-H_c(i))^2, \text{ summed over all } i$$

Again, S may be normalized using any known method so as to fall, for example, within a range such as [0,1].

U.S. Pat. No. 5,594,807 describes still other methods for quantifying the similarity between $H_{ref}$ and $H_c$ that include weighting of the absolute error sums, as well as calculation of the fourth moment (kurtosis) of the differences. These methods may be used in this invention as well—all that is required is that some predetermined measure S of similarity between $H_{ref}$ and $H_c$ be computed, for example, in a block comparison module 127 in the processing system.

One should keep in mind that "similarity" here has nothing to do with image quality as such, but rather with how likely it is that the current pixel block represents structure as opposed to a region of speckle. Consequently, $S(H_{ref}, H_c)$ can also be thought of as a "block property value" or "structure likelihood measure" or function, where the value S=0 (as defined in either case above) indicates almost certain speckle and S=1 indicates with near certainty a highly specular body structure such as bone.

Let $s(i,j,k)=S(H_{ref}, H_c)$ calculated for the pixel at location (i,j,k). Regardless of how $S(H_{ref}, H_c)$ is defined and computed in any given implementation of the invention, the "structure likelihood" value s(i,j,k) for each pixel (or each pixel block, depending on whether histograms are compiled for volumes around each pixel in the interrogation region or only for entire blocks throughout the interrogation region) is then preferably stored in a corresponding memory space 176. At this point, the entire interrogation region will have two representations: the brightness values b(i,j,k) and the structure likelihood values s(i,j,k).

3-D Speckle Suppression

According to the invention, the structure likelihood value s(i,j,k) (or, equivalently, "speckle score") of each pixel (or block, depending on whether the interrogation region is pre-partitioned into pixel blocks) in the interrogation region is compared with a predetermined threshold value. If $s(i,j,k)$ is less than the threshold, then the corresponding pixel is assumed to lie either in a region of speckle, or in a region with characteristics similar enough to speckle that it can be treated as such; the brightness value $b(i,j,k)$ of each such pixel is then reduced, that is, scaled down, for example, by any experimentally predetermined amount such as 20% or 30%. The "scaling factor" for other pixels whose structure likelihood value is greater than or equal to the threshold is set to one, that is, these values are left unchanged. Each pixel whose $s(i,j,k)$ is less than the threshold is therefore "de-emphasized" or "suppressed." Simple scaling down by a fixed factor each pixel whose respective $s(i,j,k)$ falls below the threshold is the preferred method because it is straight-forward and quickly calculated.

In FIG. 1, scaled brightness values $w(i,j,k)$ are shown as being stored in a dedicated memory space 178. To save memory, it would of course also be possible not to store these values, but rather to calculate them as needed. Thus, $w(i,j,k)=\beta*b(i,j,k)$, where $\beta$ is the chosen scale factor. Assuming a predetermined down-scaling factor of 30%, $\beta$ would therefore be equal to 1.0 if $s(i,j,k)$ is greater than or equal to the threshold, or to 0.7 if is not.

Note that every reduction in per-pixel calculations may lead to significant savings in computation burden given the large number of pixels in a typical 3-D interrogation region and the high frame rate for the transducers in many of the systems in which the invention will be implemented. Nonetheless, it would also be possible to use some other scaling factor that is a more complicated function of $s(i,j,k)$, with or without a threshold. For example, assuming as before that $S=0$ implies a perfect "match" between $H_{ref}$ and $H_c$, so that $H_c$ is almost certainly not a structure of interest, and that $S=1$ indicates that $H_c$ almost certainly is, one could also calculate $w(i,j,k)$ as some exponential or other function of $s(i,j,k)$, for example:

$$w(i,j,k)=\alpha*EXP(-\beta*(1-s(i,j,k))*b(i,j,k)$$

where $\alpha$ and $\beta$ are experimentally predetermined constants.

Such a scaling function would avoid the need for a "yes-or-no" threshold, but at the cost of more complicated calculations. Known fuzzy logic schemes could also be used to determine to what extent a given pixel lies in a speckle region, given $s(i,j,k)$.

3-D to 2-D Projection ("X-Ray Ultrasound")

Figure 5:
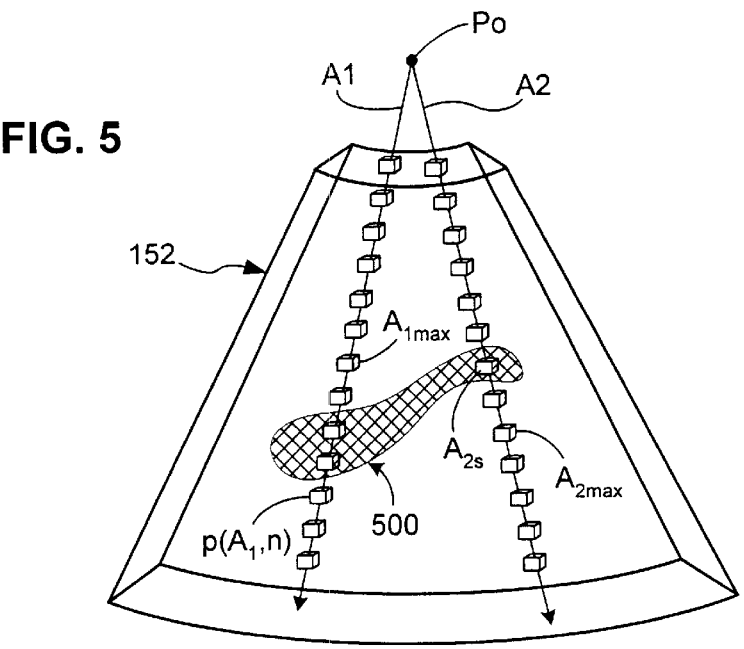
FIG. 5 illustrates imaging through a 3-D volume as in maximum intensity projection (MIP).

The 3-D interrogation region 152 is illustrated in FIG. 5, in which two view vectors (which may, for example, be receive beam lines) A1, A2 are also shown emanating from a point of origin Po, which is usually taken to be the center of the transducer array face. Along each vector, several pixels (or pixel blocks) are shown. In actual diagnostic ultrasound applications, there will of course usually be thousands of pixels per vector. Only a few are shown here merely for the sake of clarity.

Also illustrated in FIG. 5 is a speckle region 500, through which both vectors A1, A2 pass. Each pixel has a scaled brightness value $w(i,j,k)$, which will have been calculated as described above. Each pixel (and scaled value) can also be identified by the vector it lies on, and its position along that vector. Thus, the pixel marked $p(A_1,n)$ is the nth pixel along vector A1.

Figure 6:
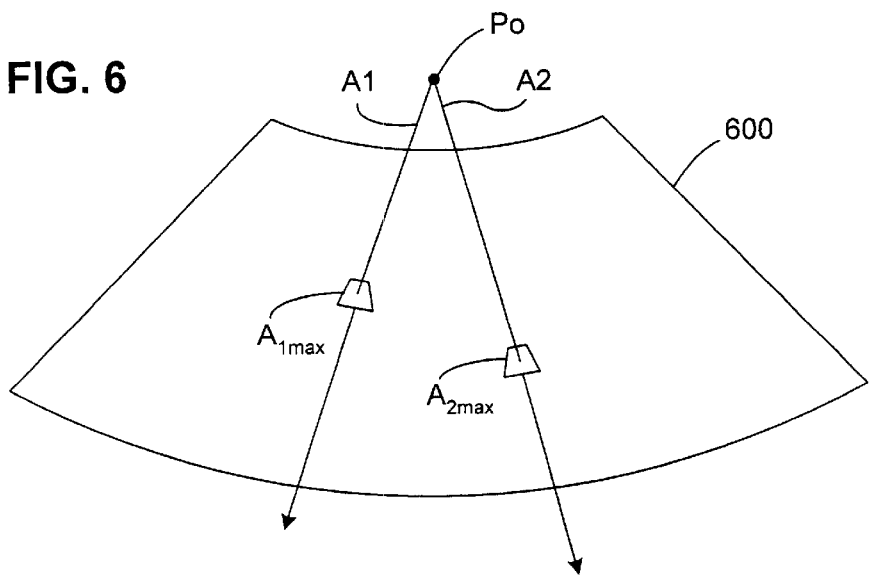
FIG. 6 illustrates projection of 3-D pixel information onto a display plane.

In the preferred embodiment of the invention, a maximum intensity projection (MIP) is calculated in the projection module 128, which also mathematically projects the 3-D image of the interrogation region onto a 2-D display plane 600 (FIG. 6). The display plane can then be scan converted as needed and displayed as the image 184 on the display screen 182.

As is known in the art, using the MIP technique, the pixel of maximum brightness (intensity) along each vector is determined, for example, simply by comparing the values along each vector. Each maximum value is then assigned to a portion of the 2-D display plane at a position where the respective vector intersects the display plane.

Now assume that there is a body structure that extends from above the speckle region 500 on vector A1 to below the speckle region 500 on vector A2. Assume further that, except for pixels lying in the speckle region 500, the maximum-intensity pixels on vectors A1 and A2 are $A_{1max}$ and $A_{2max}$ as shown in FIG. 5. Finally, assume the echo intensity of $A_{1max}$ is greater than that of the speckle region itself, but that the intensity of $A_{2max}$ is less, perhaps because of attenuation. Conventional systems that use MIP would "see" (project for display) $A_{1max}$, because its return is absolutely stronger than the speckle, but would display the brighter speckle value, for example, $A_{2s}$, rather than the much more interesting $A_{2max}$, which lies beyond the speckle region.

As is described above, however, the brightness value for the pixel corresponding to $A_{2s}$ would be scaled down. Assuming a properly chosen threshold and scaling factor, the value $A_{2s}$ will have been reduced to less than $A_{2max}$. Thus, as FIG. 6 illustrates, using the invention, the correct values $A_{1max}$ and $A_{2max}$ will be chosen as the maximum intensity values along their respective vectors, and will therefore be assigned as the values for corresponding 2-D regions on the display plane 600. The invention is thus able to "see" through the speckle region 500 to the pixels corresponding to structure, even when the speckle is very bright and even where speckle creates the strongest sensed echo signals in the entire interrogation region.

In the preferred embodiment of the invention, the MIP technique is used for projection of the 3-D scan region onto a 2-D subset suitable for display. Other known techniques may be used, however, such as volume or surface rendering. It is also possible to do without projection altogether by, for example, allowing the user to select a 2-D slice of the interrogation region using conventional input devices and display routines.

Color Coding

The projected display may also be color-coded in order to help the user see regions of structure. Note that the structure likelihood value (or, more generally "block property value") $s(i,j,k)$ does not depend on the echo intensity for that pixel, but rather on the distribution of intensity values in a region of the pixel. Thus, just because a pixel is bright does not mean it refers to structure, or to speckle. Even after scaling down of the intensity value of a pixel likely to be from speckle, the intensity value may still be greater than that for all other pixels on the same vector, even those that are from structure but are still weaker, for example, because the structure is located much deeper than the very bright speckle.

Coloring is therefore used in the preferred embodiment of the invention to further suppress the visibility of speckle in the ultimate display. In this "colorized" embodiment of the invention, the structure likelihood value $s(i,j,k)$ of each pixel that is in the 2-D, projected display plane is examined and assigned a color. Assume, for example, that all the values s(i,j,k) have been normalized to fall in a [0,1] range, with s(i,j,k)=0 indicating maximum likelihood of speckle noise. Many different coloring schemes may then be used, and can be chosen using normal design methods. Just one of many possible coloring schemes would be to assign a "rainbow" of colors to different intervals. For example, eight different colors could be chosen as follows:

| s(i,j,k) | Color |
| --- | --- |
| [0, 0.125) | Indigo |
| [0.125, 0.25) | Blue |
| [0.25, 0.375) | Teal |
| [0.375, 0.5) | Green |
| [0.5, 0.625) | Yellow |
| [0.625, 0.75) | Orange |
| [0.75, 0.875) | Red–Orange |
| [0.875, 1] | Red |

Of course, other intervals and colors may be chosen in any given implementation. The result of this color-coding will be that even bright speckle will be distinguishable in the display from even weak structure.

What is claimed is:

1. A method for imaging a region of a body comprising the following steps:
   A) generating a three-dimensional (3-D) representation of a region of interest (ROI) of the body as a 3-D pattern of image elements the region of interest corresponding to a 3-D interrogation region;
   B) assigning to each image element an intensity value corresponding to a predetermined imaging property of the image element;
   C) selecting a three-dimensional group of the image elements as a current element block;
   D) computing a block property value indicative of the likelihood that the current element block corresponds to a region of noise;
   E) repeating steps C and D for different element blocks;
   F) projecting the intensity values in the 3-D interrogation region onto a two-dimensional (2-D) display plane as a function of the block property values; and
   G) displaying a representation of the display plane on a display.

2. A method as defined in claim 1, further including the following steps:
   computing a current distribution function of the intensity values of the image elements in the current element block; and
   computing each block property value as a predetermined comparison function of the current distribution function and a reference distribution function.

3. A method as defined in claim 2, in which:
   the step of generating the 3-D representation of the ROI comprises scanning the ROI with an ultrasound transducer; and
   the predetermined imaging property is an echo strength of the ultrasound returned to the transducer from within the ROI.

4. A method as defined in claim 3, further including the following steps: determining the reference distribution function by:
   selecting a reference region of known noise;
   measuring reference noise intensity values from a plurality of points within the reference region;
   grouping the reference noise intensity values into a plurality of intervals that cover an intensity range from a minimum intensity to a maximum intensity; and
   for each interval, assigning a bin value that is a count of how many of the reference noise intensity values that lie within a corresponding interval;
   computing the current distribution function by grouping the intensity values of the image elements in the current element block into the plurality of intervals and calculating a predetermined comparison function of the plurality of current intensity values and reference noise intensity values in each interval.

5. A method as in claim 4, in which the comparison function is a function of the absolute differences between the plurality of current intensity values and the plurality of reference intensity values in each interval.

6. A method as in claim 4, in which the comparison function is a function of the sum of the squares of differences between the number of current intensity values and the number of reference intensity values in each interval.

7. A method as in claim 4, further including the following step:
   if the block property value indicates that the element block corresponds to a region of noise, scaling down the intensity values of the element block.

8. A method as in claim 4, in which the reference noise intensity values are representations of the intensity of ultrasonic echo return signals from speckle.

9. A method as in claim 4, further comprising the step of generating the reference distribution function by scanning a known speckle region.

10. A method as in claim 4, further including the following steps:
    associating a color with each of a plurality of block property value intervals;
    when displaying the representation of the display plane, rendering each image element displayed with the color associated with the block property value interval in which its corresponding block property value falls.

11. A method as in claim 1, in which the step of projecting the intensity values onto the 2-D display plane comprises generating a maximum intensity projection (MIP) of the intensity values onto the display plane, the MIP comprising:
    selecting a point of view;
    projecting a plurality of vectors from the point of view and through the three-dimensional (3-D) representation of the ROI; and
    selecting for display on the display plane the image element whose intensity value is greatest along each respective vector.

12. A method as in claim 1, in which the step of selecting the current element block and the step of repeating steps C and D for each image element comprise sequentially designating each image element in the interrogation region as a current base element and forming a respective one of the element blocks for each of the current base elements.

13. A method for imaging a region of interest (ROI) of a body comprising the following steps:
    A) scanning the ROI with an ultrasound transducer and thereby generating a three-dimensional (3-D) representation of the ROI as a 3-D pattern of image elements;
    B) assigning to each image element an intensity value corresponding to an echo strength of the ultrasound returned to the transducer from each image element within the ROI;

C) determining a reference distribution function by:
  i) selecting a reference region of known speckle noise;
  ii) measuring reference intensity values from a plurality of points within the reference region;
  iii) grouping the reference intensity values into a plurality of intervals that cover an intensity range from a minimum intensity to a maximum intensity; and
  iv) for each interval, assigning a bin value that is a count of how many of the reference intensity values that lie within the respective interval;
D) selecting a three-dimensional group of the image elements as a current element block;
E) computing a current distribution function of the intensity values of the image elements in the current element block by grouping the intensity values of the image elements in the current element block into the plurality of intervals and calculating a predetermined comparison function of the plurality of current intensity values and reference intensity values in each interval;
F) computing a block property value, indicative of the likelihood that the current element block corresponds to a region of speckle noise, by calculating a predetermined comparison function of the current distribution function and the reference distribution function;
G) repeating steps D–F for different element blocks covering the entire ROI;
H) projecting the intensity values in the 3-D ROI onto a two-dimensional (2-D) display plane as a function of the block property values; and
I) displaying a representation of the display plane on a display;
J) in which the step of projecting the intensity values onto the 2-D display plane comprises generating a maximum intensity projection (MIP) of the intensity values onto the display plane, the MIP comprising:
  i) selecting a point of view;
  ii) projecting a plurality of vectors from the point of view and through the three-dimensional (3-D) representation of the ROI; and
  iii) selecting for display on the display plane the image element whose intensity value is greatest along each respective vector.

14. An ultrasound imaging system comprising:
A) a transducer forming means for transmitting spatially focussed beams of ultrasound into a three-dimensional (3-D) region of interest (ROI) of a body and for receiving echo signals from within the ROI;
B) conversion means for converting the echo signals into a 3-D representation of the ROI as a 3-D pattern of image elements and for assigning to each image element an intensity value corresponding to a predetermined imaging property of the image element;
C) compilation means for sequentially selecting three-dimensional groups of the image elements as current element blocks;
D) comparison means for computing, for each element block, a block property value indicative of the likelihood that the current element block corresponds to a region of noise;
E) projection means for projecting the intensity values in the 3-D ROI onto a two-dimensional (2-D) display plane as a function of the block property values; and
F) display means for displaying a representation of the display plane on a display.

15. A system as defined in claim 14, in which the comparison means is further provided:
for computing a current distribution function of the intensity values of the image elements in the current element block; and
for computing each block property value as a predetermined comparison function of the current distribution function and a reference distribution function.

16. A system as defined in claim 15, in which:
the compilation means is further provided:
  for measuring reference intensity values from a plurality of points within a predetermined reference region;
  for grouping the reference intensity values into a plurality of intervals that cover an intensity range from a minimum intensity to a maximum intensity; and
  for each interval, for assigning a bin value that is a count of how many of the reference intensity values that lie within the respective interval;
the comparison means is further provided for computing the current distribution function by grouping the intensity values of the image elements in the current element block into the plurality of intervals and calculating a predetermined comparison function of the plurality of current intensity values and reference intensity values in each interval.

17. A system as in claim 16, in which the projection means is provided for generating a maximum intensity projection (MIP) onto the display plane, the MIP comprising:
selecting a point of view;
projecting a plurality of vectors from the point of view and through the three-dimensional (3-D) representation of the ROI; and
selecting for display on the display plane the image element whose intensity value is greatest along each respective vector.

18. A system as in claim 17, in which the comparison means is further provided for scaling down the intensity values of the element block before the MIP is generated if the corresponding block property value indicates that the element block corresponds to a region of noise.

* * * * *